(12) United States Patent
Galler

(10) Patent No.: US 8,272,869 B2
(45) Date of Patent: Sep. 25, 2012

(54) DENTAL MATRIX

(76) Inventor: Jeffrey Galler, Lawrence, NY (US)

( * ) Notice: Subject to any disclaimer, the term of this patent is extended or adjusted under 35 U.S.C. 154(b) by 0 days.

(21) Appl. No.: 12/955,032

(22) Filed: Nov. 29, 2010

(65) Prior Publication Data
US 2011/0262878 A1 Oct. 27, 2011

Related U.S. Application Data

(60) Provisional application No. 61/326,782, filed on Apr. 22, 2010.

(51) Int. Cl.
A61C 5/04 (2006.01)
(52) U.S. Cl. .......................................................... 433/39
(58) Field of Classification Search .......... 433/147–149, 433/156, 34, 38, 39–45
See application file for complete search history.

(56) References Cited

U.S. PATENT DOCUMENTS

| 552,697 | A | * | 1/1896 | Peterson et al. | 433/39 |
|---|---|---|---|---|---|
| 2,039,418 | A | * | 5/1936 | Hutchinson | 433/39 |
| 2,049,030 | A | * | 7/1936 | Strauss | 428/43 |
| 2,782,503 | A | * | 2/1957 | Thompson | 433/39 |
| 3,145,472 | A | * | 8/1964 | Tofflemire | 433/39 |
| 3,842,505 | A | * | 10/1974 | Eames | 433/39 |
| 5,248,258 | A | * | 9/1993 | Feldman | 433/39 |
| 5,342,194 | A | * | 8/1994 | Feldman | 433/39 |
| 5,425,635 | A | * | 6/1995 | Croll | 433/39 |
| 5,620,322 | A | * | 4/1997 | Lococo | 433/39 |
| 5,730,592 | A | * | 3/1998 | Meyer | 433/39 |
| 5,975,906 | A | * | 11/1999 | Knutson | 433/226 |
| 6,482,005 | B1 | * | 11/2002 | Summer et al. | 433/39 |
| 6,712,608 | B2 | * | 3/2004 | Bills | 433/39 |
| 7,083,412 | B1 | * | 8/2006 | Karapetyan | 433/148 |
| D605,298 | S | * | 12/2009 | McDonald | D24/181 |
| 2002/0172920 | A1 | * | 11/2002 | Bills | 433/39 |
| 2004/0152039 | A1 | * | 8/2004 | Clegg et al. | 433/39 |
| 2005/0244787 | A1 | * | 11/2005 | Summer | 433/149 |
| 2007/0148613 | A1 | * | 6/2007 | Stoll | 433/39 |
| 2009/0220912 | A1 | * | 9/2009 | Allen | 433/142 |
| 2011/0070555 | A1 | * | 3/2011 | Anderson et al. | 433/39 |

* cited by examiner

Primary Examiner — Cris L Rodriguez
Assistant Examiner — Matthew Saunders
(74) Attorney, Agent, or Firm — Gottlieb, Rackman & Reisman

(57) ABSTRACT

A dental matrix includes a band with an edge for placement toward the gingival margin of a tooth to be restored, and a strip of material such as dental floss, attached to and extending along an edge of the band. In the preferred embodiment, buccal and lingual extensions are located beyond a central portion of the band along the edge. The extensions are folded over the strip of material so as to secure the strip of dental floss to the edge. The strip of material facilitates the insertion of the band in the interproximal space between two teeth.

8 Claims, 4 Drawing Sheets

DENTAL MATRIX

RELATED APPLICATION

This application claims priority to provisional application Ser. No. 61/326,782 filed on Apr. 22, 2010 and incorporated herein by reference.

FIELD OF INVENTION

The present invention relates generally to a dental matrix. More specifically, the invention involves an improved dental matrix for use in conjunction with fillings located at the interproximal areas between adjacent teeth.

BACKGROUND OF THE INVENTION

A number of dental matrices for use in connection with filling cavities have been available for some time. Some of these matrices are specifically designed for fillings located in interproximal areas between adjacent teeth.

Normally, adjacent healthy teeth are in proximal contact with each other at a contact point. However, if a tooth experiences decay or otherwise experiences damage, its contact point with the adjacent tooth may be lost. During restoration of the tooth, therefore, it is important for a proper contact point with the adjacent tooth to be restored.

In removing decay and in restoring a decayed tooth, the dentist attempts to preserve as much natural tooth as possible and restore the tooth with a proper contact point. When posterior teeth have interproximal decay on mesial or distal surfaces, a dentist will use a hand piece to remove sufficient tooth structure to gain access to the decay, remove the decay and shape the resultant void in the tooth in preparation of filling the void. A matrix is placed interproximally and is typically wrapped around the sides of the tooth to define the desired shape of the finished tooth and to keep the filling material from flowing beyond the desired tooth boundary. A matrix typically comprises a thin metallic or plastic strip that is flexible and can be bent around the tooth being restored. A malleable filling is then placed and hardened, following which the matrix is removed.

A common problem in placing a matrix interproximally is that the tooth to be filled will often be in very tight contact with the adjacent tooth, and therefore it becomes difficult to place the matrix interproximally. This difficulty is especially pronounced when using sectional matrix strips that merely cover one interproximal wall of the affected tooth, as opposed to circumferential matrix bands that fit over and around the entire tooth somewhat more easily. Currently, dentists try to overcome this problem by cutting away additional tooth structure interproximally, thus widening the distance between the adjacent teeth so as to more easily place the matrix. However, cutting away healthy, irreplaceable tooth structure is undesirable since it is not minimally invasive.

Another method for overcoming this problem is to place a separating ring or wedge interproximally before beginning to remove the decay; in that way, by the time the preparation of the cavity is complete, a separation has been created between the adjacent teeth, so that it is now easy to place the matrix interproximally. The problem with this technique, however, is that the pre-operative presence of the ring or wedge limits visibility and accessibility for the dentist. Moreover, the separating ring or wedge must also be removed during the placement of a matrix and then replaced during the filling of a cavity causing the dentist to perform an extra step in the process.

For aiding the filling of an area located interproximally between adjacent teeth, one matrix is disclosed in U.S. Pat. No. 2,039,419 dated Jun. 11, 1934, to Hutchinson. The matrix includes a piece of sheet metal with two wire tie members. A piece of dental floss is hooked to one of the wire members so that the matrix may be inserted interproximally by first dragging the floss through the space between the adjacent teeth.

Despite its ostensible utility, this matrix suffers from a number of deficiencies. For example, the matrix does not effectively loosen the tight space between the adjacent teeth for entry of the matrix since the depth of the matrix is comprised of both the sheet metal and wire ligature. In practice, such a matrix is actually more difficult to pass through the space between the teeth since the sheet metal and wire ligature must pass through the space at once.

U.S. Pat. No. 6,712,608, to Bills, for anatomically contoured matrix bands for use in dental restoration procedures, discloses a matrix band having an asymmetrical shape to provide form for molding a dental filling into a shape that closely approximates the asymmetrical and generally trapezoidal shape of a tooth. However, this matrix is difficult to place interproximally and is used in conjunction with a separating ring during the preparation of the cavity. As mentioned above, these separating rings often cause the cavity area to be less visible and accessible to the dentist.

The prior art does not provide for a dental matrix which is easily inserted interproximally. Current matrices are difficult to insert between tight contact points. That is, prior art applications, including those referenced above, have in general provided a matrix that is bulky and difficult to insert without either cutting away additional, irreplaceable tooth structure or by first utilizing a separating ring or wedge in order to facilitate inserting the matrix between the adjacent teeth.

Thus, as is clear from the prior art, a definitive need exists for a dental matrix which may be easily inserted between adjacent teeth and which provides the proper contour for filling the cavity.

SUMMARY OF THE INVENTION

In view of the deficiencies and drawbacks in the prior art, it is a primary object of the present invention to provide a dental matrix that is adapted to effectively and efficiently be inserted between adjacent teeth so that a cavity may be filled interproximally and to provide a proper contact point with the adjacent tooth.

Another object of the present invention is to provide a dental matrix that is adapted for minimally invasive dentistry.

Yet another object of the present invention is to provide a dental matrix that is adapted for a dentist to maintain visibility and accessibility to fill a cavity.

Yet another object of the present invention is to provide a dental matrix that is adapted to fit between tight contact points without the use of a separating ring or wedge during preparation of a cavity.

Additional objectives will be apparent from the description of the invention that follows.

In accordance with my invention, in an illustrative embodiment thereof, there is provided an improved dental matrix having a piece of dental floss affixed to the edge of the inferior border of the matrix for interproximal application. The dental matrix is positioned interproximally and is then wrapped around the sides of the tooth to be restored to provide a contour for restoration.

Additional features of the invention are described below in more detail.

BRIEF DESCRIPTIONS OF THE DRAWINGS

The above-described and other advantages and features of the present disclosure will be appreciated and understood by those skilled in the art from the following detailed description and drawings, of which:

Figure 1:
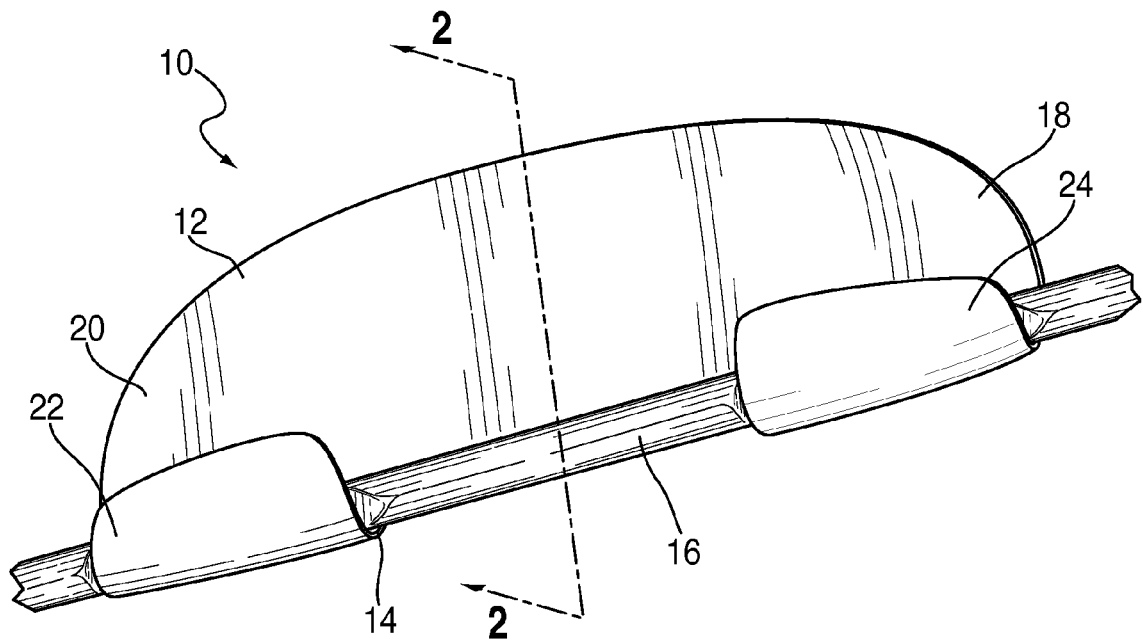
FIG. 1 is a top perspective view of the preferred embodiment of the dental matrix of the invention.
Figure 2:
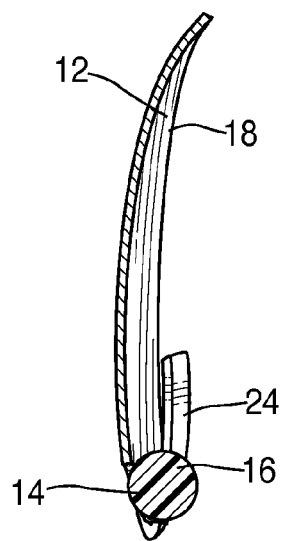
FIG. 2 is a cross-sectional view of the dental matrix of FIG. 1 taken along the line 2-2 in FIG. 1.
Figure 3:
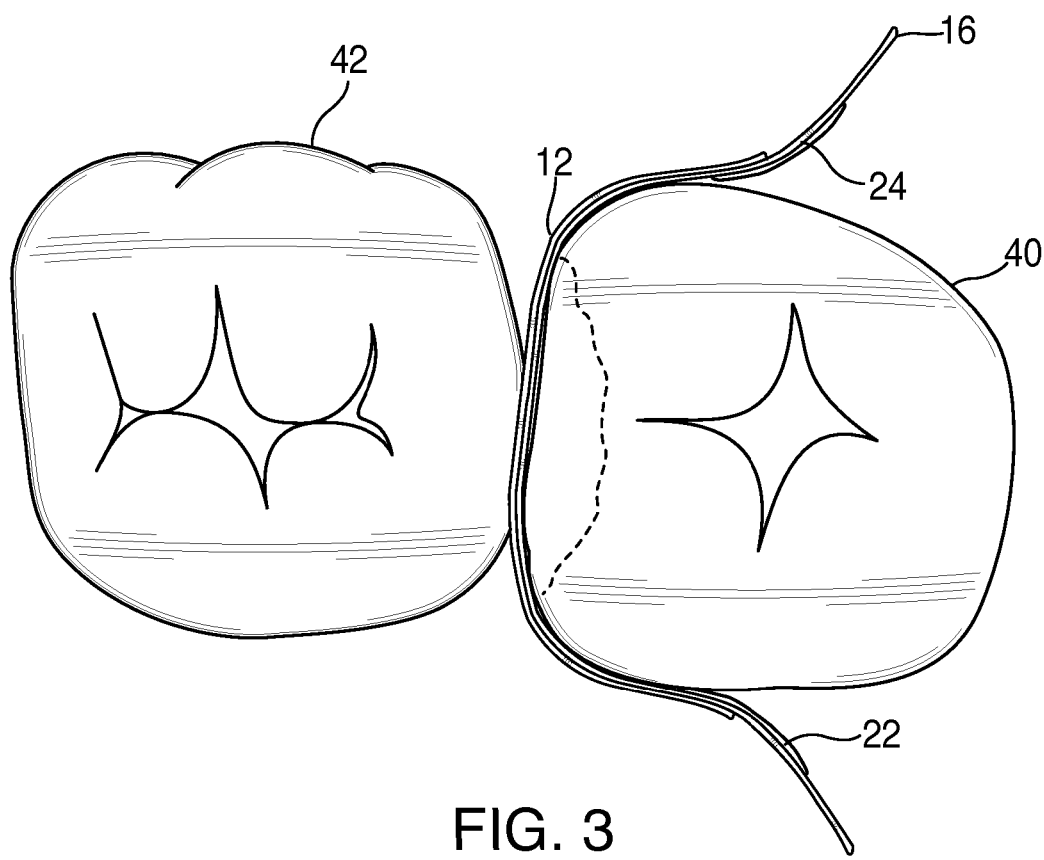
FIG. 3 is a top view of two teeth comprising two molars that shows the dental matrix of FIG. 1 disposed against a tooth having a cavity formed therein.
Figure 4:
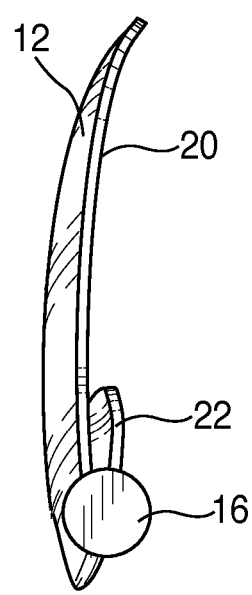
FIG. 4 is a side elevational view of the dental matrix of FIG. 1.

The above-described and other advantages and features of the present disclosure will be appreciated and understood by those skilled in the art from the following detailed description.

DETAILED DESCRIPTION OF THE INVENTION

With reference to FIGS. 1 through 4, there is shown a preferred embodiment of a dental matrix 10 of the present invention. Generally, the dental matrix 10 has a band 12 with an edge 14 for placement toward the gingival margin of the tooth 40 to be restored, and a strip 16 attached to and extending along edge 14. The band 12 is preferably formed of stainless spring steel or any other appropriate metallic, plastic or other flexible and resilient material. Stainless spring steel provides the band 12 with flexibility so that it can be molded around a tooth into a desired position. Preferably, the band 12 is a sectional band rather than a circumferential band.

The strip 16 is preferably formed of dental floss comprised of nylon filaments or plastic ribbon. Preferably, polytertafluoroethylene (PTFE) ribbon sold under the brand name Teflon® may be utilized, but other materials having an ease-of-insertion property comparable to that of dental floss such as polyethylene fibers, polylactic acid (PLA) fibers, natural fibers such as wool, flax, bamboo, synthetic fibers, soy fiber, or any combination thereof, in any proportion, may be utilized. Any other suitable fibers in appropriate combinations and proportions may be used, for example, from one or more fibers, one or more filaments, or any combination thereof, that are twisted, knitted, entangled, braided, woven, non-woven, waxed or unwaxed or otherwise processed to form a unitary monofilament strand suitable for use as dental floss.

The band 12 has properties of a standard type dental matrix with a first end 18 and an opposite end 20 of the band 12. In the preferred embodiment, the band 12 has a buccal extension 24 at the first end 18 and a lingual extension 22 at the second end 20 beyond a central portion of the band 12. The buccal extension 24 is for placement closer to the cheek and the lingual extension 22 is for placement closer to the tongue of a person's mouth. The extensions 22, 24 are folded over the strip of dental floss 16 so as to secure the strip 16 to edge 14. Although two extensions are shown in FIGS. 1 through 4, three or more extensions may be present. The central portion may be comprised of a cut out of the band 12. The length of the central portion of the band 12 is required to be less than the length of the band 12. Preferably, the length of the central portion approximates the width of the proximal point of a typical molar tooth, approximately between 3 mm and 5 mm.

The dental matrix 10 is placed interproximally to provide a contour for restoration of one of the teeth by first positioning the central portion interproximally between tooth 40 and tooth 42, following which the remaining portion of the band 12 is positioned interproximally and is then wrapped around the side of the tooth 40 to be restored. Interproximally between tooth 40 and tooth 42 is a contact point which is horizontally located where each tooth is most likely to make contact with the adjacent tooth. The contact point is located approximately two thirds of the way up from the gingival margin where the teeth 40, 42 intersect the gingiva. The occlusal plane is the plane extending over and defined by the top surfaces of the teeth 40, 42.

It is frequently difficult to place a matrix band interproximally, since the tooth to be restored is often in very tight contact with the adjacent tooth. This difficultly is especially pronounced when using sectional matrix bands that merely cover one interproximal wall of the tooth to be restored, as opposed to circumferential matrix bands that fit over and around the entire tooth.

Separating rings or wedges before removing the decay are commonly used to temporarily create a space between adjacent teeth so that the dental matrix will slip in more easily. Such separating rings or wedges often cause the operating site to be less visible and less accessible for the dentist. Accordingly, by providing dental matrix 10 comprising a band with a strip of dental floss along the edge, the placement of a separating ring or wedge prior to preparing the cavity for restoration is no longer necessary since dental floss will almost always slip in between the very tightest contact points. After preparing the cavity and placing the dental matrix 10, any of the various separating rings or wedges can be placed in the usual fashion to keep the matrix in intimate contact with the tooth, prevent extrusion of excess filling material, and to temporarily create a space between the tooth to be filled and the adjacent tooth, so that after placing the filling and removing the matrix, the subsequent filling will be in tight contact with the adjacent tooth.

Figure 5:
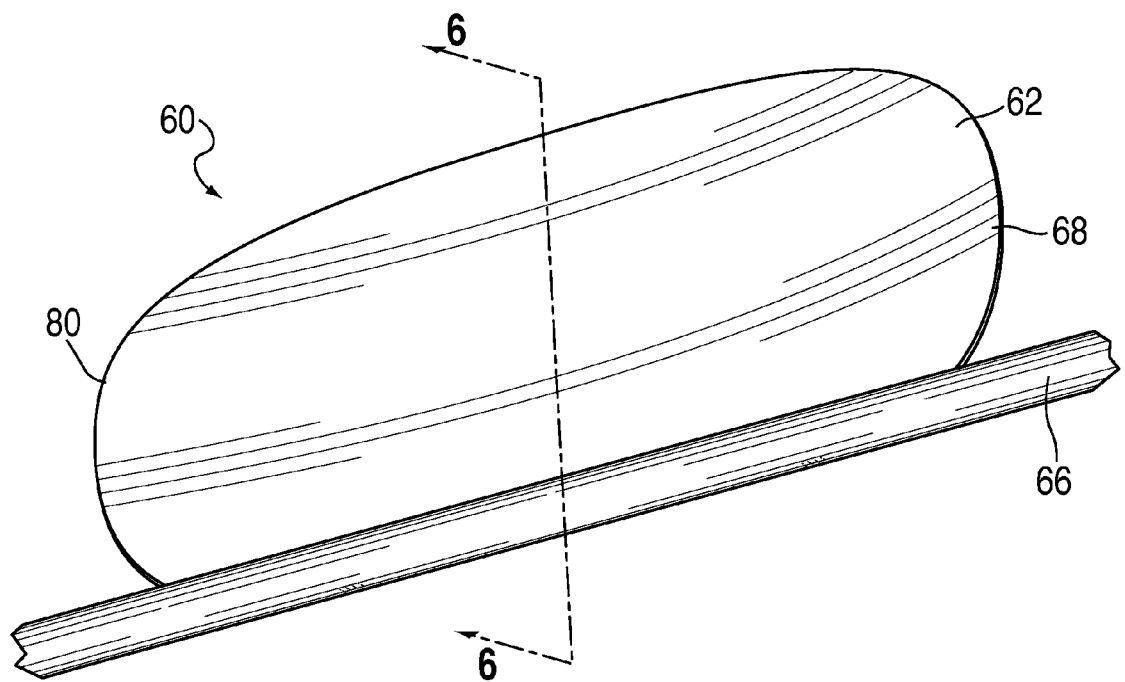
FIG. 5 is a top perspective view of an alternative embodiment of a dental matrix of the invention.
Figure 6:
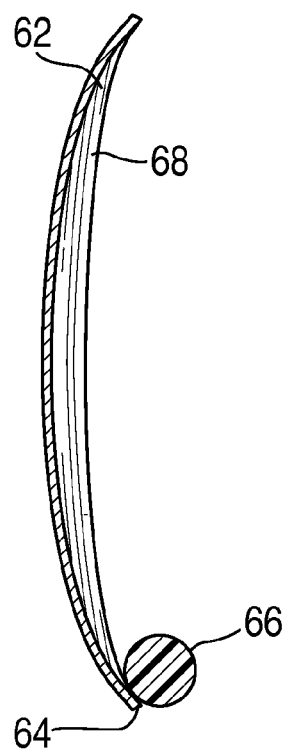
FIG. 6 is a cross-sectional view of the dental matrix of FIG. 5 taken along the line 6-6 in FIG. 5.
Figure 7:
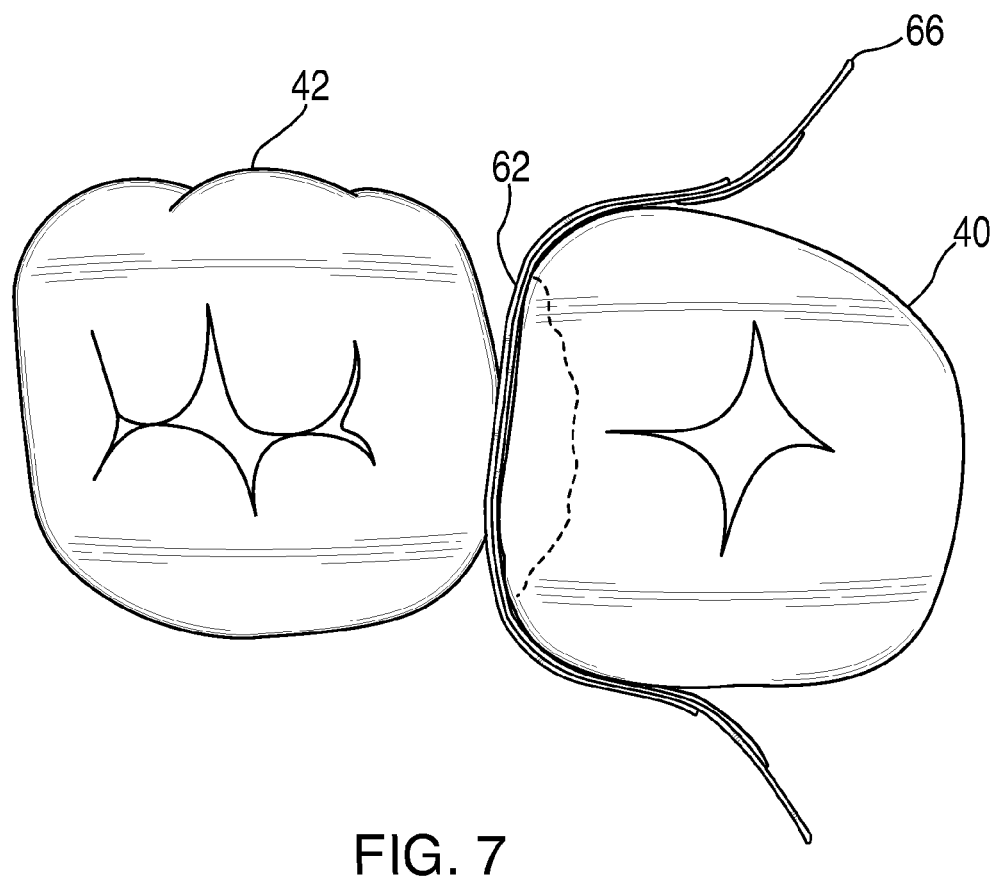
FIG. 7 is a top view of two teeth comprising two molars that shows the dental matrix of FIG. 6 disposed against a tooth having a cavity formed therein.

With reference to FIGS. 5-7, there is shown another embodiment of the present invention. Generally, the dental matrix 60 has a band 62 with an edge 64 for placement toward the gingival margin of the tooth 40 to be restored, and a strip 66 attached to and extending along edge 64. In the alternative embodiment, the strip 66 is secured along the edge 64 of the band 62 at each end 68, 80 of a central portion of the band 62. The strip 66 may be secured to the ends 68, 80 of the central portion by any means sufficient to attach the strip 66, such as adhesives, epoxy, sealing, cement or connectors. Preferably, the strip 66 is attached to the ends 68, 80 by methacrylate adhesive.

The accompanying drawings only illustrate a dental matrix and its constituent parts, however, other types and styles are possible, and the drawings are not intended to be limiting in that regard. Thus, although the description above and accompanying drawings contain much specificity, the detail provided should not be considered as limiting the scope of the invention but merely as providing illustrations of some of the presently preferred embodiments. The drawings and the description are not to be taken as restrictive on the scope of the invention and are understood as broad and general teachings in accordance with the present invention. While the present embodiments of the invention have been described using specific terms, such description is for present illustrative purposes only, and it is to be understood that modifications and variations to such embodiments, including but not limited to the substitutions of equivalent features, materials, or parts, may be practiced by those of ordinary skill in the art without departing from the spirit and scope of the invention.

What I claim is:

1. A dental matrix for interproximal placement between two teeth of a patient to provide a contour for restoration of one of the teeth, the dental matrix comprising:
    a metal or plastic band with an edge for placement toward the gingival margin of the tooth to be restored;
    a strip of dental floss attached to and extending along said edge and being exposed so that said strip enters the interproximal space between two teeth before said band to facilitate insertion and interproximal positioning of the matrix; and
    a respective securing member on said edge at each end of a central portion of the band for securing the strip of dental floss to said edge.

2. A dental matrix in accordance with claim 1 wherein the band has buccal and lingual extensions beyond a central portion of the band along said edge, said extensions being folded over the strip of dental floss so as to secure the strip of dental floss to said edge.

3. A dental matrix for interproximal placement between two teeth of a patient to provide a contour for restoration of one of the teeth, the dental matrix comprising:
    a metal or plastic band with an edge for placement toward the gingival margin of the tooth to be restored;
    a strip of dental floss attached to and extending along said edge and being exposed so that said strip enters the interproximal space between two teeth before said band to facilitate insertion and interproximal positioning of the matrix; and
    a securing element along said edge at at least each end of a central portion of the band for securing the strip of dental floss to said edge.

4. A dental matrix for interproximal placement between two teeth of a patient to provide a contour for restoration of one of the teeth, the dental matrix comprising;
    a metal or plastic band with an edge for placement toward the gingival margin of the tooth to be restored;
    a strip of material attached to and extending along said edge, said strip of material being exposed along said edge to facilitate interproximal positioning of the edge; and
    a securing member along said edge at each end of a central portion of the band for securing the ends of said strip of material to said edge.

5. A dental matrix in accordance with claim 3 wherein the band has buccal and lingual extensions beyond a central portion of the band along said edge, said extensions being folded over the said strip of material so as to secure the strip of material to said edge.

6. A dental matrix of claim 3 wherein said strip of material is arranged along at least a portion of the edge to enter between the interproximal space between two of the teeth prior to the band to facilitate the introduction of the band into said interproximal space.

7. A dental matrix of claim 4 wherein said strip of material is positioned to enter between said two teeth before said band as said matrix is advanced toward the gingival margin.

8. A dental matrix for interproximal placement between two teeth of a patient to provide a contour for restoration of one of the teeth, the dental matrix comprising;
    a metal or plastic band with an edge for placement toward the gingival margin of the tooth to be restored;
        a strip of material attached to and extending along said edge, said strip of material being exposed along said edge to facilitate interproximal positioning of the edge; wherein said strip of material is positioned to enter between said two teeth before said band as said matrix is advanced toward the gingival margin.

* * * * *